US009000035B2

(12) United States Patent
Hughes

(10) Patent No.: US 9,000,035 B2
(45) Date of Patent: *Apr. 7, 2015

(54) TREATMENT OF OBESITY USING NON-DAILY ADMINISTRATION OF 6-O-(4-DIMETHYLAMINOETHOXY) CINNAMOYL FUMAGILLOL

(71) Applicant: Zafgen, Inc., Cambridge, MA (US)

(72) Inventor: Thomas E. Hughes, Boston, MA (US)

(73) Assignee: Zafgen, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/056,829

(22) Filed: Oct. 17, 2013

(65) Prior Publication Data

US 2014/0045935 A1 Feb. 13, 2014

Related U.S. Application Data

(63) Continuation of application No. 13/990,271, filed as application No. PCT/US2011/062413 on Nov. 29, 2011.

(60) Provisional application No. 61/417,692, filed on Nov. 29, 2010, provisional application No. 61/500,662, filed on Jun. 24, 2011.

(51) Int. Cl.
*A01N 43/20* (2006.01)
*A01N 43/24* (2006.01)
*A01N 37/44* (2006.01)
*A01N 37/02* (2006.01)
*A61K 31/335* (2006.01)
*A61K 31/24* (2006.01)
*A61K 31/22* (2006.01)
*A61K 31/336* (2006.01)

(52) U.S. Cl.
CPC ..................... *A61K 31/336* (2013.01)

(58) Field of Classification Search
None
See application file for complete search history.

(56) References Cited

U.S. PATENT DOCUMENTS

| | | |
|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Eustache et al. |
| 6,989,392 B2 | 1/2006 | Collins et al. |
| 7,084,108 B2 | 8/2006 | Olson et al. |
| 7,268,111 B2 | 9/2007 | Olson et al. |
| 7,718,695 B2 | 5/2010 | Kim et al. |
| 8,349,891 B2 | 1/2013 | Crawford et al. |
| 8,367,721 B2 * | 2/2013 | Hughes et al. ................. 514/475 |
| 2003/0220371 A1 | 11/2003 | Kallander et al. |
| 2004/0067266 A1 | 4/2004 | Toppo |
| 2004/0116495 A1 | 6/2004 | Marino Jr. et al. |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 * | 2/2012 | Hughes et al. ............. 424/158.1 |
| 2012/0322867 A1 | 12/2012 | Hughes et al. |
| 2013/0018095 A1 * | 1/2013 | Vath .............................. 514/475 |

FOREIGN PATENT DOCUMENTS

| | | |
|---|---|---|
| EP | 0682020 A1 | 11/1995 |
| WO | WO-99/59986 A1 | 11/1999 |

(Continued)

OTHER PUBLICATIONS

Kim et al. Development of parenteral formulation for a novel angiogenesis inhibitor, CKD-732 through complexation with hydroxypropyl-beta-cyclodextrin. International Journal of Pharmaceutics, 272, 2004: 79-89.*

(Continued)

*Primary Examiner* — Anna Pagonakis
(74) *Attorney, Agent, or Firm* — Goodwin Procter LLP

(57) ABSTRACT

The invention generally relates to methods of treating an overweight or obese subject, and treating overweight- or obesity-related conditions using non-daily administration of e.g, a MetAP-2 inhibitor.

12 Claims, 10 Drawing Sheets

(56) References Cited

FOREIGN PATENT DOCUMENTS

| | | |
|---|---|---|
| WO | WO-99/59987 A1 | 11/1999 |
| WO | WO-00/64876 A1 | 11/2000 |
| WO | WO-03/027104 A1 | 4/2003 |
| WO | WO-2004/033419 A1 | 4/2004 |
| WO | WO-2005/082349 A1 | 9/2005 |
| WO | WO-2006/080591 A1 | 8/2006 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/051318 A1 | 4/2012 |
| WO | WO-2012/064838 A1 | 5/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |

OTHER PUBLICATIONS

Anderson, Hamilton H., "The Use of Fumagillin in Amoebiasis," *Annals New York Academy of Sciences*, 1118-1124.

Benny, Ofra, et al., (2008) "An Orally Delivered Small-Molecule Formulation with Antiangiogenic and Anticancer Activity," *Nature Biotechnology*, 26, 7:799-807.

Bernier et al. (2005) "Fumagillin class inhibitors of methionine aminopeptidase-2," *Drugs of the Future* 30(5): 497-500.

Brakenhielm, E., et al., (2004) "Angiogenesis Inhibitor, TNP-470, Prevents Diet-Induced and Genetic Obesity in Mice," *Circulation Research*, http://circres.ahajournals.org (accessed on Feb. 8, 2007).

Braunwald, et al.. "Obesity" in Harrison's Principles of Internal Medicine, 15th Ed., 479-86 (2001).

Didier, Peter J., et al. (2006) "Antimicrosporidial Activities of Fumagillin, TNP-470, Ovalicin, and Ovalicin Derivatives in Vitro and in Vivo," *Antimicrobial Agents and Chemotherapy*, p. 2146-2155.

DiPaolo, J.A., et al. (1958-1959) "Studies on the Carcinolytic Activity of Fumagillin and Some of its Derivatives," *Antibiotics Annual*, 541-546.

Drevs, Joachim, et al. (2003) "Antiangiogenic Potency of FK866/K22.175, a New Inhibitor of Intracellular NAD Biosynthesis, in Murine Renal Cell Carcinoma," *Anticancer Research* 23: 4853-4858.

Dumas, J., et al., "Synthesis and Structure Activity Relationships of Novel Small Molecule Cathepsin D Inhibitors," *Bioorganic & Medicinal Chemistry Letters* 9 (1999) 2531-2536.

Eder, JP, et al., (2006) "Phase 1 Dose Escalation Safety & Tolerance Study of PPI-2458 in Subjects with Non-Hodgkin's Lymphoma or Solid Tumors," (Presented on Nov. 7-10, 2006 at EORTC-NCI-AACR Symposium on "Molecular Targets and Cancer Therapeutics.").

Everhart (1993) "Contributions of Obesity and Weight Loss to Gallstone Disease," *Ann Intern Med*. 119:1029-1035.

Ingber et al. (1990) "Synthetic analogues of fumagillin that inhibit angiogenesis and suppress tumour growth," *Nature* 348: 555-557.

Jeong, et al., "Total Synthesis and Antiangiogenic Activity of Cyclopentane Analogues of Fumagillol," *Bioorg. Med. Chem. Lett*. 15 3580-83 (2005).

Kim, YM, et al. (2007) "Assessment of the Anti-Obesity Effects of the TNP-470 Analog, CKD-732," *Journal of Molecular Endocrinology* 38, 455-465.

Kruger, Erwin, A., (2000) "TNP-470: An Angiogenesis Inhibitor in Clinical Development for Cancer," *Exp. Opin. Invest. Drugs* 9(6), pp. 1383-1396.

Masiero, Laura, et al. (1997) "New Anti-angiogenesis Agents: Review of the Clinical Experience with Carboxyamido-Triazole (CAI), Thalidomide, TNP-470 and Interleukin-12," *Angiogenesis*, 1: 23-35.

McCowan, Max C., et al., (1951) Fumagillin (H-3), a New Antibiotic with Amebicidal Properties, *Science*, vol. 113, p. 202-203.

Milkowski, Deborah M., et al., *Antiangiogenic Agents in Cancer Therapy*, Chapter 22 "TNP-470," pp. 385-398.

Molina et al. (1997) "Potential Efficacy of Fumagillin in Intestinal Microsporidiosis Due to Enterocytozoon Bieneusi in Patients with HIV Infection: Results of a Drug Screening Study," *AIDS*, 11:1603-1610.

Molina et al. (2002) "Fumagillin Treatment of Intestinal Microsporidiosis," *N. Engl. J. Med*. 346(25): 1963-1969.

Molina, et al.(2000) "Trial of Oral Fumagillin for the Treatment of Intestinal Microsporidiosis in Patients with HIV Infection," *AIDS*, 14:1341-1348.

Naganuma, Yasuko, et al. (2011) "Metronomic Doxifluridine Chemotherapy Combined with the Anti-Angiogenic Agent TNP=470 Inhibits the Growth of Human Uterine Carcinosarcoma Xenografts," *Cancer Sci* 102(8): pp. 1545-1552.

National Task Force on the Prevention and Treatment of Obesity (1993) "Very Low-Calorie Diets," *JAMA* 270(8):967-974.

Noel et al. (2009) "Increased Risk of Acute Pancreatitis and Biliary Disease Observed in Patients with Type 2 Diabetes," *Diabetes Care* 32(5):834-838.

Pagliarulo et al. (2003) "Gallstone disease and related risk factors in a large cohort of diabetic patients," *Digestive and Liver Disease* 36:130-134.

Picoul et al. (2003) "Progress in fumagillin synthesis," *Pure Appl. Chem*. 75(2-3): 235-249.

Rupnick, MA (2002) "Adipose Tissue Mass Can be Regulated Through the Vasculature," *PNA* 99, 10730-10735.

Seneca et al. (1956) "Amebiasis: a review. II. Laboratory diagnosis, differential diagnosis and therapy," *Am J. Digestive Dis*. 1: 310-322.

International Search Report and Written Opinion for PCT/US2011/062413, mailed Feb. 17, 2012 (8 pages).

Shin, SJ (2010) "A Phase I Pharmacokinetic and Pharmacodynamic Stdy of CKD-732, an Antiangiogenic Agent, in Patients with Refractory Solid Cancer," Invest New Drugs 28:650-658.

Weinsier et al. (1993) "Gallstone Formation and Weight Loss," *Obesity Research* 1(1):51-56.

Weinsier, et al. (1995) "Medically Safe Rate of Weight Loss for the Treatment of Obesity: A Guideline Based on Risk of Gallstone Formation " *The American Journal of Medicine* 98:115-117.

Winter et al. (2006) "Endothelial $\alpha_v\beta 3$ Integrin-Targeted Fumagillin Nanoparticles Inhibit Angiogenesis in Atherosclerosis," *Arterioscler Thromb Vasc Biol*.: 2103-2109.

Yanai, Shigeo, et al. (1995) "Antitumor Effect of Arterial Administration of a Medium-Chain Triglyceride Solutionof an Angiogenesis Inhibitor, TNP-470, in Rabbits Bearing VX-2 Carcinoma," *Pharmaceutical Research* 12(5): pp. 653-657.

Yanai, Shigeo, et al., (1994) "Antitumor Activity of a Medium-Chain Triglyceride Solution of the Angiogenesis Inhibitor TNP-470 (AGM-1470) when Administered Via the Hepatic Artery to Rats Bearing Walker 256 Carcinosarcoma in the Liver," The Journal of Pharmacology and Experimental Therapeutics 271(3): pp. 1267-1273.

Lijnen, H.R., et al. (2010) "Fumagillin Reduces Adipose Tissue Formation in Murine Models of Nutritionally Induced Obesity," Obesity 18: 2241-2246.

Teicher, et al (1999) "Antiangiogenic Agents in Cancer Therapy" pp. 385-398.

Garrabrant et al. (2004) "Small molecule inhibitors of methionine aminopeptidase type 2 (MetAP-2) fail to inhibit endothelial cell proliferation or formation of microvessels from rat aortic rings in vitro," *Angiogenesis* 7:91-96.

(56) References Cited

OTHER PUBLICATIONS

Chun et al. (2005) "Novel inhibitors targeted to methionine aminopeptidase 2 (MetAP2) strongly inhibit the growth of cancers in xenografted nude model," *Int J Cancer* 114(1):124-30.

Han et al. (2000) "Design and Synthesis of Highly Potent Fumagillin Analogues from Homology Modeling for a Human MetAP-2," *Bioorganic & Medicinal Chemistry Letters* 10:39-43.

Kim et al. (2004) "Development of parenteral formulation for a novel angiogenesis inhibitor, CKD-732 through complexation with hydroxypropyl-beta-cyclodextrin," *Int J Pharm.* 272(1-2):79-89.

Kim et al. (2005) "General pharmacology of CKD-732, a new anti-cancer agent: effects on central nervous, cardiovascular, and respiratory system," *Biol Pharm Bull.* 28(2):217-23.

Lee et al. (2004) "Absorption, distribution, metabolism, and excretion of CKD-732, a novel antiangiogenic fumagillin derivative, in rats, mice, and dogs," *Arch Pharm Res.* 27(2):265-72.

Lee et al. (2006) "Selective N-demethylation of tertiary aminofumagillols with selenium dioxide via a non-classical Polonovski type reaction," *Heterocycles* 68(5):915-932.

Lee et al. (2007) "Design, Synthesis, and Antiangiogenic Effects of a Series of Potent Novel Fumagillin Analogues," *Chem. Pharm. Bull.* 55(7) 1024-1029.

Myung et al. (2002) "The identification of in vitro metabolites of CKD-732 by liquid chromatography/tandem mass spectrometry," *Rapid Commun Mass Spectrom.* 16(21):2048-53.

Rhee et al. (2009) Angiogenesis inhibitor attenuates parathyroid hormone-induced anabolic effect, *Biomed Pharmacother.* 63(1):63-8.

Shin et al. (2012) "A Phase 1b pharmacokinetic study of the anti-angiogenic agent CKD-732 used in combination with capecitabine and oxaliplatin (XELOX) in metastatic colorectal cancer patients who progressed on irinotecan-based chemotherapy," *Investigational New Drugs* 30(2):672-680. (Published Online Dec. 29, 2010).

Srikumar et al. (2012) "Structural insights on Brugia malayi transglutaminase with cinnamoyl derivatives—a molecular docking approach " *International Journal of Pharma and Bio Sciences* 3(3):998-1006.

\* cited by examiner

TREATMENT OF OBESITY USING NON-DAILY ADMINISTRATION OF 6-O-(4-DIMETHYLAMINOETHOXY) CINNAMOYL FUMAGILLOL

CROSS REFERENCE TO RELATED APPLICATIONS

This application is a continuation of U.S. patent application Ser. No. 13/990,271, filed May 29, 2013, which is a U.S. national phase application under 35 U.S.C. §371 of International Application No. PCT/US2011/062413, filed Nov. 29, 2011, which claims the benefit of and priority to U.S. Provisional Patent Application No. 61/417,692, filed Nov. 29, 2010, and U.S. Provisional Patent Application No. 61/500,662, filed Jun. 24, 2011, the contents of each of which are hereby incorporated by reference in their entirety.

BACKGROUND

Obesity is a complex medical disorder of appetite regulation and metabolism resulting in excessive accumulation of adipose tissue mass. Typically defined as a body mass index (BMI) of 30 kg/m$^2$ or more, obesity is a world-wide public health concern that is associated with cardiovascular disease, diabetes, certain cancers, respiratory complications, osteoarthritis, gallbladder disease, decreased life expectancy, and work disability. The primary goals of obesity therapy are to reduce excess body weight, improve or prevent obesity-related morbidity and mortality, and maintain long-term weight loss.

Treatment modalities typically include diet and exercise programs, lifestyle management, pharmacotherapy, and surgery. Treatment decisions are made based on severity of obesity, seriousness of associated medical conditions, patient risk status, and patient expectations. Notable improvements in cardiovascular risk and the incidence of diabetes have been observed with weight loss of 5-10% of body weight, supporting clinical guidelines for the treatment of obesity that recommend a target threshold of 10% reduction in body weight from baseline values. These improvements are notable even for patients who may be overweight (with a BMI of 27 kg/m$^2$) but also have a weight related co-morbidity such as hypertension, type 2 diabetes, dyslipidemia, or central adiposity.

However, while prescription anti-obesity medications are typically considered for selected patients at increased medical risk because of their weight and for whom lifestyle modifications (diet restriction, physical activity, and behavior therapy) alone have failed to produce durable weight loss, approved drugs have had unsatisfactory efficacy for severely obese subjects, leading to only ~3-5% reduction in body weight after a year of treatment.

Bariatric surgery may be considered as a weight loss intervention for patients at or exceeding a BMI of 40 kg/m$^2$. Patients with a BMI≥35 kg/m$^2$ and an associated serious medical condition are also candidates for this treatment option. Recently the US-FDA has approved lapband procedures for patients exceeding a BMI of 35 kg/m$^2$ and for those patients who are 30 kg/m$^2$ or higher who have at least one obesity-related condition, such as diabetes. Unfortunately, postoperative complications commonly result from bariatric surgical procedures, including bleeding, embolism or thrombosis, wound complications, deep infections, pulmonary complications, and gastrointestinal obstruction; reoperation during the postoperative period is sometimes necessary to address these complications. Rates of reoperation or conversion surgery beyond the postoperative period depend on the type of bariatric procedure, and in one study ranged from 17% to 31%. Intestinal absorptive abnormalities, such as micronutrient deficiency and protein-calorie malnutrition, also are typically seen with bypass procedures, requiring lifelong nutrient supplementation. Major and serious adverse outcomes associated with bariatric surgery are common, observed in approximately 4 percent of procedures performed (including death in 0.3 to 2 percent of all patients receiving laparoscopic banding or bypass surgeries, respectively)

MetAP2 encodes a protein that functions at least in part by enzymatically removing the amino terminal methionine residue from certain newly translated proteins such as glyceraldehyde-3-phosphate dehydrogenase (Warder et al. (2008) J Proteome Res 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res. 63:7861) and infectious diseases such as microsporidiosis, leishmaniasis, and malaria (Zhang et al. (2002) J. Biomed. Sci. 9:34). However, such MetAP2 inhibitors may be useful as well for patients with excess adiposity and conditions related to adiposity including type 2 diabetes, hepatic steatosis, and cardiovascular disease (via e.g. ameliorating insulin resistance, reducing hepatic lipid content, and reducing cardiac workload). Methods of treating obese subjects that are more effective than e.g. dieting alone are clearly needed.

SUMMARY OF THE INVENTION

This disclosure generally relates to methods of treating an overweight or obese subject or patient that include non-daily administration of a pharmaceutically effective amount of a MetAP2-inhibitor, such as 6-O-(4-dimethylaminoethoxy) cinnamoyl fumagillol or pharmaceutically acceptable salts thereof, to a patient in need thereof, e.g., a human or a companion animal such as a cat or a dog. For example, a method for treating obesity or for reducing body weight in a patient in need thereof is provided, comprising administering to the patient, on a less than daily basis, a dose of a formulation comprising a therapeutically effective amount of a compound 6-O-(4-dimethylaminoethoxy)cinnamoyl fumagillol or pharmaceutically acceptable salts thereof. Such a method, upon a single initial administration of a dose or after administration of two doses, may provide the patient with a body weight loss of about 0.3 to about 2 kg of the initial patient weight. Such a disclosed method may provide a well tolerated rate of weight loss of about 1 to about 1.5% of the initial patient weight per week.

Contemplated methods may include administering to the patient a single dose of a disclosed formulation about every other day, twice weekly, about once a week, about once every other week, and/or about once or twice a month.

A method for treating obesity or for reducing body weight in a patient in need thereof is provided herein that includes administering to the patient a dose of a formulation comprising a therapeutically effective amount of a compound 6-O-(4-dimethylaminoethoxy)cinnamoyl fumagillol or pharmaceutically acceptable salts thereof, for a first period of time, withheld for a second period of time, and again administered for a third period of time, wherein the therapeutically effective amount provides the patient with a body weight loss of for example, about 1% to about 2% initial patient weight per week (and/or provides for a body weight loss of about 0.5 kg to about 2 kg or more) after the first period of time. A first period of time may be selected from the group consisting of daily, every other day, every three, four or five days, twice weekly, or monthly. A second period of time may be selected from the group consisting of one, two, three, four, five, or six days, one, two, three, four, or five weeks, and one month. A third period of time may be selected from daily, every other day, every three, four or five days, twice weekly, monthly, or every other month.

Contemplated doses may include therapeutically effective amount of the disclosed compound of e.g., about 0.5 mg/m$^2$ to about 3 mg/m$^2$ (based on a patient's actual or calculated surface area), e.g. about 0.9 mg/m$^2$ to about 1.5 mg/m$^2$, e.g., about 1.25, 1.5, 2 or 3 mg/m$^2$. In other embodiments, a therapeutically effective amount of a disclosed compound may be at least about 20 to about 80 µg per kg, or at least about of 20 to about 40 µg per kg excess body weight of the patient. For example, a therapeutically effective amount of a disclosed compound, e.g., administered every three or four days may be a dosage that includes e.g., about 1.8 mg, 2.5 mg, 2 mg, 3 mg, 4 mg, 5 mg, or 6 mg of a disclosed compound. Administration of a single dose with such a method may reduce weight in the patient for at least three or four days, or up to seven days, for example, even without further administration.

Disclosed methods may include maintaining from 0 to 0.3 ng/mL of the compound in the plasma of a patient for at least 12 hours to 24 hours or more after administration of a dose, but for example, no longer than about 36 hours after administration. It may be understood that disclosed methods may include repeatedly administering to the patient an effective dose on a less than daily basis until a desired weight is achieved.

For example, provided herein is a method for treating obesity or for reducing body weight in a patient in need thereof, comprising administering to the patient a dose comprising about 0.9 mg/m$^2$ or more (e.g., about 0.75 mg/m$^2$ to about 3 mg/m$^2$), of a compound 6-O-(4-dimethylaminoethoxy)cinnamoyl fumagillol or pharmaceutically acceptable salts thereof, wherein, for example, a single administration of the dose reduces weight in the patient for at least three days or at least four days.

Disclosed methods may include administering about 20 µg to about 80 µg of the compound per excess body weight of the patient. For example, a method for treating obesity or for reducing body weight is provided that comprises administering to a patient in need thereof at least about 30 µg or at least about 40 µg (e.g., at least about 40 µg to about 60 µg) of 6-O-(4-dimethylaminoethoxy)cinnamoyl fumagillol or pharmaceutically acceptable salts thereof per kg of excess adipose tissue of the patient. In an embodiment, a method of reducing the body weight of a patient in need thereof for at least four days is provided comprising administering to the patient a single dose of at least about 20 µg of 6-O-(4-dimethylaminoethoxy)cinnamoyl fumagillol or pharmaceutically acceptable salts thereof, per kg of excess adipose tissue of the patient. Such a method may further comprises administering a second dose (e.g., at intervals of two, three or four days or more) of at least about 40 µg of 6-O-(4-dimethylaminoethoxy)cinnamoyl fumagillol or pharmaceutically acceptable salts thereof, per kg of excess body weight of the patient at least about 2 days after administration of the single dose. A disclosed method may further comprise administering subsequent doses at intervals of between about 4 days and 1 month, and/or may comprise maintaining about 0 to about 0.3 ng/mL of the compound in the plasma of a patient for 24 hours after administration, e.g., for about 24 to about 36 hours after administration.

A method for treating obesity or for reducing body weight in a patient in need thereof is also provided comprising administering to the patient, on a less than daily basis, a dose of a formulation comprising a therapeutically effective amount of a compound 6-O-(4-dimethylaminoethoxy)cinnamoyl fumagillol or pharmaceutically acceptable salts thereof, wherein the method produces less testes-related toxicity as compared to a patient administered the dose on a daily basis.

In some embodiments, a disclosed method may provide, upon administration, adiponectin levels in the patient that are increased by at least 50% above the adiponectin level in the patient before administration. Contemplated human patients may have an initial body mass index of at least about 27 kg/m$^2$, at least about 30 kg/m$^2$, or at least about 35, or at least about 40 kg/m$^2$. Administering as contemplated herein may comprise subcutaneous administration or intravenous administration.

For example, provided herein is a method for treating obesity in a patient having an initial body mass index of at least about 30 kg/m$^2$, comprising administering to the patient (e.g. human), on a less than daily basis (e.g. twice weekly, weekly, or every 3 or 4 days) a dose of a formulation comprising a therapeutically effective amount of a compound 6-O-(4-dimethylaminoethoxy)cinnamoylfumagillol or pharmaceutically acceptable salts thereof, as well as a method for reducing the weight of a patient (e.g. human) having an initial body mass index of at least about 27 kg/m$^2$, and suffering from weight related co-morbidity (e.g., hypertension, type 2 diabetes, dyslipidemia, and/or central adiposity), comprising administering to the patient, on a less than daily basis e.g. twice weekly, weekly, or every 3 or 4 days, a dose of a formulation comprising a therapeutically effective amount of a compound 6-O-(4-dimethylaminoethoxy)cinnamoylfumagillol or pharmaceutically acceptable salts thereof. The dose comprises about 0.5 mg/m$^2$ to about 1.5 mg/m$^2$ of the compound, or about 30 µg to about 90 µg of the compound per kilogram of excess body weight of the patient, about 20 µg to 60 µg about per kilogram of ideal body weight of the patient, or 1.5 to about 6.0 mg of the free base of the compound.

Also provided herein is a pharmaceutically acceptable formulation comprising a compound 6-O-(4-dimethylaminoethoxy)cinnamoyl fumagillol or pharmaceutically acceptable salts thereof; wherein a single dose parenteral administration of the formulation to a human patient produces a peak plasma concentration ($C_{max}$) of about 0.5 to about 14 ng/m, or a peak plasma concentration may be about 0.5 to about 6 ng/mL. In some embodiments, the minimum plasma concentration ($C_{min}$) 24 hours after the administration is about 0 to about 0.3 ng/mL. In an embodiment, the minimum plasma concentration in a patient 36 hours after administration is de minimus, or not detectable, e.g. about 0 ng/mL.

A pharmaceutically acceptable formulation is contemplated that includes a compound 6-O-(4-dimethylaminoethoxy)cinnamoyl fumagillol or pharmaceutically acceptable salts thereof; wherein a single dose parenteral (e.g. intravenous or subcutaneous) administration of the formulation to a human patient produces a minimum plasma concentration ($C_{min}$) 24 hours after administration of about 0 to about 0.3 ng/mL. Such single dose administration to a human may produce a mean area under the curve concentration of the compound of (AUC (0-24 hours) of about 6 to about 30 ng hr/mL, or about 8.6 to about 13.9 ng hr/mL.

DETAILED DESCRIPTION

Overview

Figure 1:
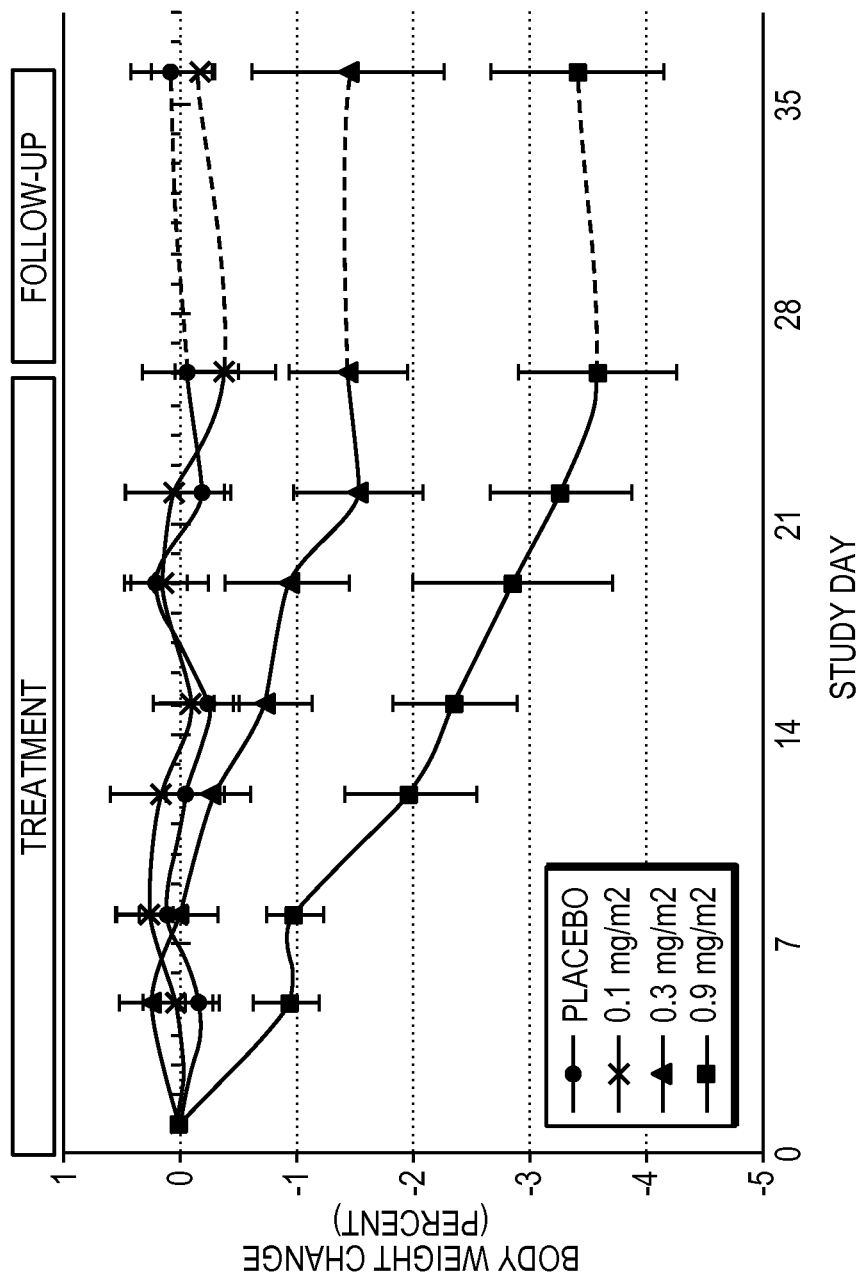
FIG. 1 depicts body weight change (percent) with twice weekly dosing of 0.1 mg/m$^2$, 0.3 mg/m$^2$, and 0.9 mg/m$^2$ (approximately 1.8 to 2.1 mg) of 6-O-(4-dimethylaminoethoxy)cinnamoyl fumagillol in human patients. Values are means±SEM (n=6 per dose level study); p values derived from 2-way ANOVA with Bonferroni post-test comparisons (*, p<0.05; , p<0.01; *, p<0.001 vs. placebo).

The disclosure in part relates to treatment of e.g., obesity using less than daily dosing and arises in part due to the unexpected discovery that the effectiveness of the drug remains for several days after administration of an initial dose, even though the half life of the drug is shorter than one day, together with the additional unexpected discovery that dosing and/or effectiveness of the drug depends on the amount of excess body weight of an overweight patient, rather than total body weight of the patient.

Obesity and being overweight refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, degree of excess body fat, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using the formulas: SI units: BMI=weight (kg)/(height$^2$(m$^2$), or US units: BMI=(weight(lb)*703)/ (height$^2$(in$^2$).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. For children, the definitions of overweight and obese take into account age, stature, and gender as they relate to what are appropriate amounts of body fat and do not strictly rely upon BMI calculations.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat, and intra-abdominal, or visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male. Methods of determining whether a subject is overweight or obese that account for the ratio of excess adipose tissue to lean body mass may involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink. Yet another method is fan-beam dual energy X-ray absorptiometry (DEXA). DEXA allows body composition, particularly total body fat and/or regional fat mass, to be determined non-invasively.

Excess body weight may be assessed, for example, by comparing the weight of a patient in need of treatment to the weight of the same patient that would achieve a desired, e.g. non-obese, BMI (e.g. a desired BMI of about 25 or less). For example, excess body weight of a 1.6 m patient weighing 89.6 kg (and having a BMI of 35) may be found by calculating the weight required for a BMI of 25 (i.e., about 64 kg); the initial excess body weight of such patient would about 89.6-64=25.6 kg. Ideal body weight can be assessed, for example, by calculating 25*(height of patient), or e.g., by consulting Metropolitan or other life insurance tables.

Methods

A method for treating obesity or for reducing body weight in a patient in need thereof is provided herein, comprising administering to the patient, on a less than daily basis, a dose of a formulation comprising a therapeutically effective amount of a compound 6-O-(4-dimethylaminoethoxy)cinnamoyl fumagillol or pharmaceutically acceptable salts thereof. Such methods may include administering to the patient a single dose of the formulation about every other day (e.g. every 2 days); twice weekly (e.g. every 3 days, every 4 days, every 5 days, every 6 days, or e.g. administered with an interval of about 2 to about 3 days between doses), once a week, every other week, twice monthly, once a month or even less often. In some embodiments, contemplated methods include administering a single dose no more than twice weekly, e.g. no more than every other day or e.g., every third day. It may be appreciated that methods that include administering a single dose on a less frequent basis, may, in some embodiments, be a method directed to maintaining a specific weight, such as a more optimal body weight after treatment using other methods disclosed herein. Disclosed methods may include administering a dose of a disclosed compound on a less than daily basis until a desired weight is achieved.

In another embodiment, provided herein is a method for treating obesity or for reducing body weight in a patient in need thereof, comprising administering to the patient a dose of a formulation comprising a therapeutically effective amount of a compound 6-O-(4-dimethylaminoethoxy)cinnamoyl fumagillol or pharmaceutically acceptable salts thereof, for a first period of time, withheld for a second period of time, and again optionally administered for a third period of time, e.g., alternate dosing regimens. For example, for the first period of time a patient may be administered a disclosed formulation daily, every other day, every three, four or five days, twice weekly, weekly, twice monthly, monthly, or yearly; during the second period of time (e.g. 1 day, 1 week, 2 weeks, 1 month) no dose is administered; and during e.g. a third period of time, the patient may be administered on a regimen similar or different to the first period of time, for example, every other day, every three, four or five days, biweekly, monthly, or yearly. At each administration or period time, the route of administration may be different or the same as another period of time.

A method for treating obesity or for reducing body weight in a patient in need thereof is also provided comprising administering to the patient, on a less than daily basis, a dose of a formulation comprising a therapeutically effective amount of a compound 6-O-(4-dimethylaminoethoxy)cinnamoyl fumagillol or pharmaceutically acceptable salts thereof, wherein the method produces less testes-related toxicity as compared to a patient administered the dose on a daily basis. For example, disclosed methods of administering a single dose of a disclosed compound on a less than daily basis may have no (or minimal) testicular tissue (e.g. seminal vesicle or testes) weigh effects, while daily administration (of e.g., the same single dose) may result in testicular lesions and/or organ weight effects.

For example, provided herein, in an embodiment, is a method for treating obesity in a patient having an initial body mass index of at least about 30 kg/m$^2$, comprising administering a dose of the disclosed compound, on a less than daily basis (e.g., every three or four days, or twice weekly) to the patient. In another embodiment, provided herein is a method for reducing the weight of a patient having an initial body mass index of about 27 kg/m$^2$ and a co-morbidity, comprising administering a dose of the disclosed compound, on a less than daily basis (e.g., every three or four days, or twice weekly) to the patient. Such methods may provide for weight loss by the patient of about 1 kg to 1.5 kg per week. Contemplated doses, administered on a less than daily basis, may be a fixed dose, for example, about 1 mg, 2 mg, 1.5 mg, 1.8 mg, 2.5 mg, 3.0 mg, 4 mg, 5 mg or even 6 mg.

The therapeutically effective amount administered in the disclosed methods such as those above may provide a patient with a body weight loss of about 0.3% to about 2%, about 0.4% to about 2%, or about 0.5% to about 2% or more, or about 0.5 kg to about 2 kg or more of the initial patient weight even after an initial dose, or after administration of two doses, or after administering after an first period of time, e.g., such methods may incur weight loss for three or four days or more after administration (e.g. parenteral (for example intravenous) administration) of a single dose. For example, a patient, after receiving a first dose and/or after receiving a subsequent dose, may continue to lose weight for three or four days or more without further administration of a disclosed compound. In some embodiments, administration of an initial first dose, or administration of a first and second dose (e.g., both administered in the same week), may provide about 0.5 kg to about 2 kg or more of weight loss. Subsequent administration may result in further weight loss, until a target patient weight is achieved.

Therapeutically effective doses may be calculated, for example, on the basis of body surface area (BSA), which can be determined using formulae such as those described by Mosteller (Mosteller RD, *N Engl J Med* 1987 Oct. 22; 317 (17):1098), in which BSA is calculated in SI units as BSA (m$^2$)=([Height(cm)×Weight(kg)]/3600)$^{1/2}$ (e.g. BSA=SQRT ((cm*kg)/3600)), or US units, in which BSA (m$^2$)=([Height (in)×Weight(lbs)]/3131)$^{1/2}$. In some embodiments, the therapeutically effective amount administered (e.g., intravenously) to patient using a disclosed method is about 0.5 mg/m$^2$ to about 1.5 mg/m$^2$, or about 0.9 mg/m$^2$ (or approximately 10 to 20 μg per kilo of total body weight) or more of a disclosed compound. In other embodiments, a therapeutically effective amount is based on excess body weight (or excess adipose tissue), for example, at least about 30 μg of a disclosed compound per kg of excess adipose tissue, (or excess body weight) of the patient, or least about 40 μg per kg or more of excess adipose tissue, (or excess body weight) of the patient, e.g., about 30 μg per kg of excess adipose tissue (or excess body weight) to about 60 μg per kg, about 40 μg per kg to about 60 μg per kg, or about 35 μg per kg to about 45 μg per kg, or about 35 μg per kg to about 50 μg per kg of excess adipose tissue (or excess body weight).

For example, provided herein is a method for treating obesity or for reducing body weight in a patient in need thereof, comprising administering to the patient a dose comprising about 0.9 mg/m$^2$ or more (about 0.75 mg/m$^2$ to about 3 mg/m$^2$, or about 0.9 mg/m$^2$ to about 1.5 mg/m$^2$) (e.g., administered intravenously) of a compound 6-O-(4-dimethylaminoethoxy)cinnamoyl fumagillol or pharmaceutically acceptable salts thereof, wherein a single administration of the dose reduces weight in the patient for at least four days.

In another embodiment, a method of treating obesity in a patient in need thereof is provided, comprising administering an effective amount of a MetAP-2 inhibitor, wherein the effective amount is proportional to excess body weight of said patient. For example, in some embodiments, such effective amount may not be proportional to total body weight. A method of treating obesity in a patient in need thereof is also provided, comprising determining the excess body weight or excess adipose tissue of said patient; determining an effective dose of a MetAP-2 based on the excess body weight or adipose tissue for said patient; and administering the effective dose to said patient.

For example, provided herein is a method for treating obesity or for reducing body weight, comprising administering to a patient in need thereof at least about 20 μg, 30 μg, or at least about 40 μg or more (e.g., about 20 μg to about 80 μg, or about 40 μg to about 60 μg) of 6-O-(4-dimethylaminoethoxy)cinnamoyl fumagillol or pharmaceutically acceptable salts thereof per kg of excess adipose tissue (or excess body weight) or, in other embodiments, about 0.9 mg/m$^2$ (e.g., of calculated surface area), or more (e.g., about 0.75 mg/m$^2$ to about 3 mg/m$^2$), of the patient.

In another embodiment, a method of treating obesity or for reducing body weight is provided comprising administering a dose, on a less than weekly basis, of 6-O-(4-dimethylaminoethoxy)cinnamoyl fumagillol or pharmaceutically acceptable salts wherein the doses comprises at least about 35 µg to about 75 µg per kilogram, about 20 to about 60 µg/kg ideal body weight, or about 20 to about 40 µg/kg of the compound per ideal body weight of the patient, wherein ideal body weight is 25*(patient height in meters).

Disclosed methods may reduce the body weight of the patient for at least 3 or at least 4 days after administration, or at least 7 days after administration, at least 14 days after administration, or even at least 1 month after administration, e.g., without further administration of the compound during that time. It is understood that even though an administration may provide for weight loss e.g. at least for 3 or 4 days, a disclosed compound may be administered more frequently, e.g. every other day.

For example, provided herein is a method of reducing the body weight of a patient in need thereof for at least four days, comprising administering (e.g., parenterally administering) to the patient a single dose of at least about 40 µg of 6-O-(4-dimethylaminoethoxy)cinnamoyl fumagillol or pharmaceutically acceptable salts thereof, per kg of excess adipose tissue of the patient. In some embodiments, such methods may further include administering a second dose of at least about 20 µg of 6-O-(4-dimethylaminoethoxy)cinnamoyl fumagillol or pharmaceutically acceptable salts thereof, per kg of excess body weight of the patient (or, in other embodiments, about 0.9 mg/m$^2$ or more (or about 0.75 mg/m$^2$ to about 3 mg/m$^2$) at least about 4 days after administration of the single dose. A second dose, for example, may be administered at intervals of three or four days or more. In another embodiments, disclosed methods may further include administering subsequent doses of a MetAP2 inhibitor (e.g. –O-(4-dimethylaminoethoxy)cinnamoyl fumagillol) at intervals of between about 4 days and 1 month. Such disclosed methods may, upon administration, increase the adiponectin levels of the patient by at least 50% above, or at least 20%, at least 30% at least 40%, or more, e.g. at least about 20% to about 60% above the adiponectin level in the patient before administration (e.g. baseline adiponectin of the patient before treatment.)

In another aspect, a method of treating obesity in a patient in need thereof is provided comprising administering to a patient an effective amount of an MetAP-2 inhibitor, wherein the effective amount is capable of increasing adiponectin levels in the patient by at least 50% above, at least 60% above, or at least 20%, at least 30% at least 40%, or more, e.g. at least about 20% to about 60%, or the adiponectin level in the patient before administration of the inhibitor. Such an effective amount of the MetAP-2 inhibitor may reduce the ratio of leptin to adiponectin plasma levels in the patient after administration. Further, therapeutically effective doses contemplated herein will not typically induce any clinically significant anti-angiogenic action.

Also provided herein is a method of optimizing weight loss in a patient undergoing weight loss treatment, comprising a) administering an amount of a MetAP-2 inhibitor to said patient; b) determining the increase in adiponectin in said patient; and c) increasing the amount of the MetAP-2 inhibitor administered to the patient if the change in adiponectin in the patient is less than an increase of about 60% or more (or 50% or more, e.g. 30% to about 60% as compared to the adiponectin level of the patient before administration of the MetAP-2 inhibitor.

In another embodiment, a method of optimizing weight loss in a patient undergoing weight loss treatment, comprising a) administering an amount of a MetAP-2 inhibitor to said patient; b) determining the increase in adiponectin in said patient; c) increasing the amount of the MetAP-2 inhibitor administered to the patient if a reduction in the ratio of leptin to adiponectin in the plasma of the patient is not greater than 50%, or not greater than 40%, e.g., the reduction of the ratio of leptin to adiponection is reduced by about 10%, 20%, 30% or 40%.

Contemplated patients include humans or companion animals (e.g. dog or cat). In some embodiments, patients may be female (e.g., in an embodiment, women of non-child bearing potential) or male (e.g., in an embodiment, surgically or biologically sterile males).

In addition to being overweight or obese, a patient may be suffering from other overweight- or obesity-related co-morbidities, i.e., diseases and other adverse health conditions associated with, exacerbated by, or precipitated by being overweight or obese. Because being overweight or obese is associated with other adverse health conditions or co-morbidities, for example diabetes, administering a disclosed MetAP2 inhibitor may bring a benefit in ameliorating, arresting development of or, in some cases, even eliminating, these overweight- or obesity-related conditions or co-morbidities. For example, contemplated methods of reducing body weight disclosed herein includes treatment those patients who have e.g., a BMI of greater than 27 kg/m$^2$, and who have one or more weight related co-morbidities, such as hypertension, type 2 diabetes, dyslipidemia, and/or central adiposity.

In some embodiments, methods provided herein may further include administering at least one other agent in addition to a disclosed MetAP2 inhibitor, e.g., an agent directed to treatment of these overweight- or obesity-related conditions.

Contemplated other agents include those administered to treat type 2 diabetes such as sulfonylureas (e.g., chlorpropamide, glipizide, glyburide, glimepiride); meglitinides (e.g., repaglinide and nateglinide); biguanides (e.g., metformin); thiazolidinediones (rosiglitazone, troglitazone, and pioglitazone); glucagon-like 1 peptide mimetics (e.g. exenatide and liraglutide); sodium-glucose cotransporter inhibitors (e.g., dapagliflozin), renin inhibitors, and alpha-glucosidase inhibitors (e.g., acarbose and meglitol), and/or those administered to treat cardiac disorders and conditions, such hypertension, dyslipidemia, ischemic heart disease, cardiomyopathy, cardiac infarction, stroke, venous thromboembolic disease and pulmonary hypertension, which have been linked to overweight or obesity, for example, chlorthalidone; hydrochlorothiazide; indapamide, metolazone; loop diuretics (e.g., bumetanide, ethacrynic acid, furosemide, lasix, torsemide); potassium-sparing agents (e.g., amiloride hydrochloride, spironolactone, and triamterene); peripheral agents (e.g., reserpine); central alpha-agonists (e.g., clonidine hydrochloride, guanabenz acetate, guanfacine hydrochloride, and methyldopa); alpha-blockers (e.g., doxazosin mesylate, prazosin hydrochloride, and terazosin hydrochloride); beta-blockers (e.g., acebutolol, atenolol, betaxolol, nisoprolol fumarate, carteolol hydrochloride, metoprolol tartrate, metoprolol succinate, Nadolol, penbutolol sulfate, pindolol, propranolol hydrochloride, and timolol maleate); combined alpha- and beta-blockers (e.g., carvedilol and labetalol hydrochloride); direct vasodilators (e.g., hydralazine hydrochloride and minoxidil); calcium antagonists (e.g., diltiazem hydrochloride and verapamil hydrochloride); dihydropyridines (e.g., amlodipine besylate, felodipine, isradipine, nicardipine, nifedipine, and nisoldipine); ACE inhibitors (benazepril hydrochloride, captopril, enalapril maleate, fosinopril sodium, lisinopril, moexipril, quinapril hydrochloride, ramipril, trandolapril); angiotensin II receptor blockers (e.g., losartan potassium, valsartan, and Irbesartan); and combinations thereof, as well as statins such as mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin, typically for treatment of dyslipidemia.

Other agents that may be co-administered (e.g. sequentially or simultaneously) include agents administered to treat ischemic heart disease including statins, nitrates (e.g., Isosorbide Dinitrate and Isosorbide Mononitrate), beta-blockers, and calcium channel antagonists, agents administered to treat cardiomyopathy including inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers, agents administered to treat cardiac infarction including ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase), agents administered to treat strokes including anti-platelet agents (e.g., Aspirin, Clopidogrel, Dipyridamole, and Ticlopidine), anticoagulant agents (e.g., Heparin), and thrombolytic agents, agents administered to treat venous thromboembolic disease including anti-platelet agents, anticoagulant agents, and thrombolytic agents, agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil, agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex, agents administered to treat sleep apnea include Modafinil and amphetamines, agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents, agentsadministered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid, agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax), agents administered to treat polycystic ovary syndrome include insulin-sensitizers, combinations of synthetic estrogen and progesterone, Spironolactone, Eflornithine, and Clomiphene, agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone, agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta, agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic, agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate), agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers, and other weight loss agents, including serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, and topamax.

In some embodiments, contemplated methods may further comprise assessing one or more indices of on-going weight loss, e.g. the ketone body production level in a patient; and optionally adjusting the amount administered; thereby optimizing the therapeutic efficacy of said MetAP2 inhibitor.

Formulations

Contemplated administration of Met-AP2 inhibitors in the disclosed methods include subcutaneous or intravenous administration. For example, injectable preparations are contemplated herein, for example, sterile injectable aqueous or oleaginous suspensions may be formulated according to the known art using suitable dispersing or wetting agents and suspending agents.

Disclosed or contemplated treatment regimens can include a corrective phase, during which a MetAP2 inhibitor dose sufficient to provide reduction of excess adiposity is administered, followed by a maintenance phase, during which a lower or equivalent MetAP2 inhibitor dose sufficient to prevent re-development of excess adiposity may be administered.

In an embodiment, a pharmaceutically acceptable formulation is provided that includes a compound 6-O-(4-dimethylaminoethoxy)cinnamoyl fumagillol or pharmaceutically acceptable salts thereof; wherein a single dose administration of the formulation to a human patient produces a peak plasma concentration ($C_{max}$) of about 0.5 to about 14 ng/mL, about 0.5 to about 6 ng/mL, for example, the peak plasma concentration is about 2.1 ng/mL. Further, provided here is a pharmaceutically acceptable formulation is provided that includes a compound 6-O-(4-dimethylaminoethoxy)cinnamoyl fumagillol or pharmaceutically acceptable salts thereof; wherein a single dose administration of the formulation to a human patient produces a $C_{min}$ about 24 hours after administration of about 0 to about 0.3 ng/mL, about 0.0 to about 0.15 ng/mL, or about 0.03 to about 0.11 ng/mL, for example, about 0.07 ng/mL, for about 36 hours or less. For example, at 36 hours after a dosage administration, the plasma concentration in a patient is about 0, or undetectable using standard detection protocols as appreciated by those skilled in the art.

For example, provided herein is a pharmaceutically acceptable formulation that includes 6-O-(4-dimethylaminoethoxy) cinnamoyl fumagillol or pharmaceutically acceptable salts wherein the single dose administration (e.g. by subcutaneous or intravenous routes) to a human produces a mean area under the curve concentration of the compound of (AUC (0-24 hours) of about 6 ng hr/mL. to about 12 ng hr/mL, 7.5 ng hr/mL to about 13.5 ng hr/mL, or about 6 ng hr/mL. to about 15 ng hr/mL, e.g. about 10.5 hr*ng/mL. In an embodiment, the mean area under the curve concentration of the compound (AUC (0-∞) after administration in a patient is about 6 ng hr/mL. to about 16 ng hr/mL, 7.6 ng hr/mL. to about 4.4 ng hr/mL, or about 9.3 ng hr/mL. to about 12.7 ng hr/mL, e.g. about 11 ng hr/mL.

EXAMPLES

The examples which follow are intended in no way to limit the scope of this invention but are provided to illustrate aspects of the disclosed methods. Many other embodiments of this invention will be apparent to one skilled in the art. Unless specified, amounts or weights of the compound refer to the weight of the free base.

Example 1

Less than Weekly Administration of a MetAP2 Inhibitor to Obese Humans

Obese patients were treated in three cohorts with intravenous administration of a formulation of the compound 6-O-(4-dimethylaminoethoxy)cinnamoyl fumagillol oxalate. The compound was intravenously administered to each patient of a cohort (except for a placebo cohort) twice weekly for 26 days. Each of patients in the three non-placebo cohorts received either 0.1 mg/m² (cohort 1); 0.3 mg/m² (cohort 2); or 0.9 mg/m² (cohort 3) doses of the compound at the time of administration. The trial was conducted under the appropriate government and medical supervision.

Weight reduction occurred for 4 days after single administration of 0.9 mg/m2 dose, despite terminal half life of the drug of only 5.4 hours ($T_{1/2}$ (H) λz (terminal) is 5.41±2.82 in cohort 3), indicating daily administration is not needed. Table 1 summarizes body weight determination of the 9 patients in the 0.9 mg/m² cohort on the day of the first dose and prior to a second dose administered three or four days later.

TABLE 1

| Subject No. | Starting weight (kg) | Ending weight (kg) | Weight Change (kg) | Weight Change (%) |
|---|---|---|---|---|
| 1 | 96.3 | 95.7 | −0.6 | −0.6 |
| 2 | 101.5 | 100.4 | −1.1 | −1.1 |
| 3 | 104.6 | 103.7 | −0.9 | −0.9 |
| 4 | 102.4 | 100.5 | −1.9 | −1.9 |
| 5 | 108.6 | 107.5 | −1.1 | −1.0 |
| 6 | 107.9 | 107.9 | 0 | 0.0 |
| 7 | 105.5 | 105 | −0.5 | −0.5 |
| 8 | 118.7 | 118 | −0.7 | −0.6 |
| 9 | 96 | 96.2 | 0.2 | 0.2 |
| Average | 104.6 | 103.9 | −0.7 | −0.7 |
| SEM | 2.3 | 2.3 | 0.0 | 0.2 |
| P | | | 0.004 | 0.004 |

Figure 2:
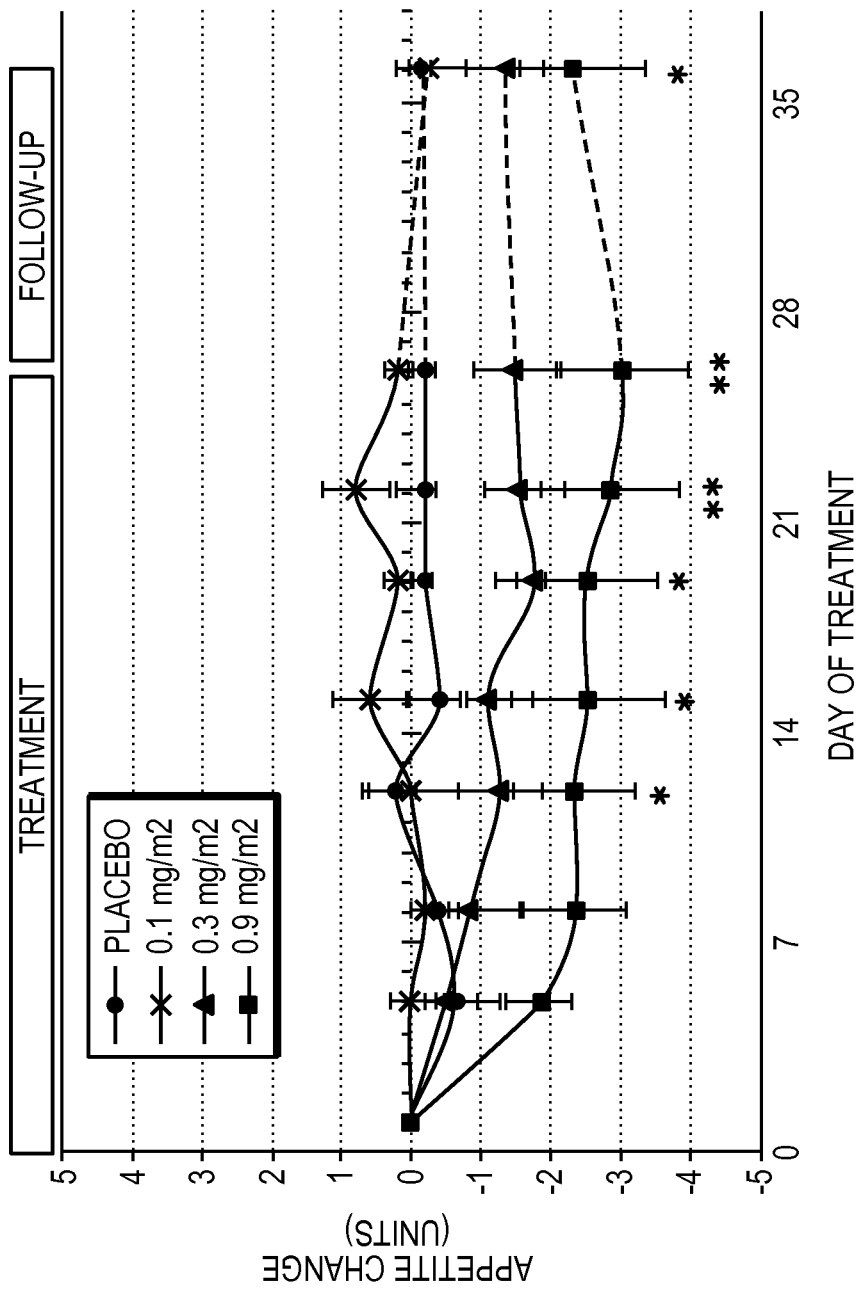
FIG. 2 depicts visual analogue scale of hunger decline by approximately 50% with body weight change (percent) with twice weekly dosing off 0.1 mg/m$^2$, 0.3 mg/m$^2$, and 0.9 mg/m$^2$ (approximately 1.8 to 2.1 mg) of 6-O-(4-dimethylaminoethoxy)cinnamoyl fumagillol in human patients. Values are means (n=6 per dose level) of changes in fasted Visual Analog Scale scores for each visit day vs. Day 1 for population; p values derived from 2-way ANOVA with Bonferroni post-test comparisons (*, p<0.05; **, p<0.01 vs. placebo).

Of the 9 subjects treated at the 0.9 mg/m² dose level, 7 patients showed greater than 3-4 percent body weight loss over 26 days of exposure. FIG. 1 depicts the body weight change (loss) as a percent before each administration of the twice weekly dose for the 0.9 mg/m² cohort. FIG. 2 depicts the Visual Analog Scale reports of hunger decline about 50% following successive biweekly dose administration for the 0.9 mg/m² cohort. As shown in FIGS. 1 and 2, a follow up check at day 36 was conducted; patients were weighed again at this 36 day mark and the weight loss from the twice weekly regimen over 26 days was substantially sustained.

Figure 3:
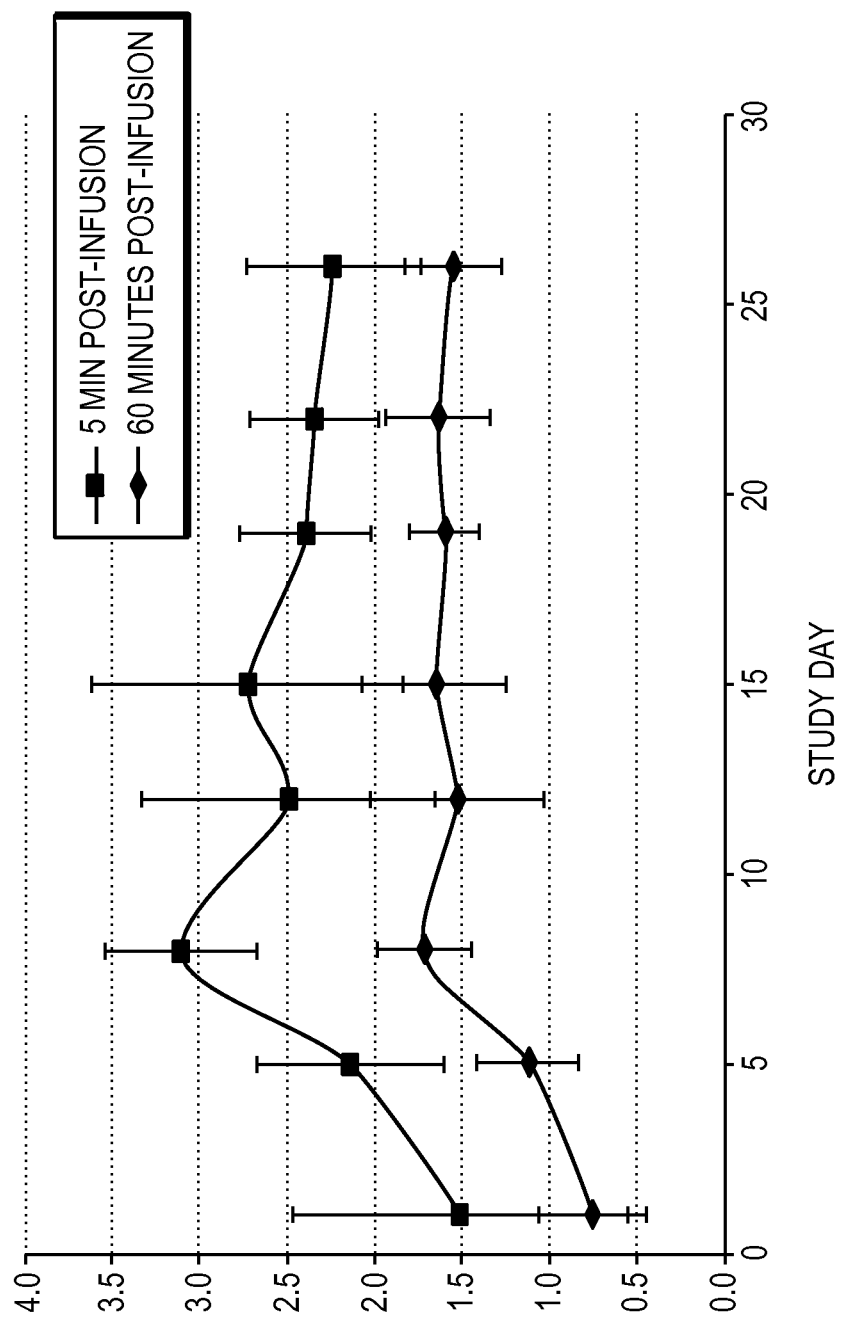
FIG. 3 depicts dose exposure stability. Y-axis is plasma concentration of compound in ng/mL trials of participants receiving 0.9 mg/m$^2$.

The average $C_{max}$ in cohort 3 was 2.1 ng/mL (with a standard deviation of 0.51 ng/mL); average $C_{min}$ was 0.07 ng/mL (SD of 0.04 ng/mL, with a measured range of 0.014-0.15 ng/mL (including poor responder), and 0.045 to 0.15 (excluding poor responder)); average AUC (0-24 hr) was 10.5 hour*ng/mL (standard deviation 1.5 hour*ng/mL, measured range 8.57 to 13.6 hr*ng/mL) and average AUC (0-∞) was 11 hour*ng/mL (SD 1.7 hour*ng/mL). FIG. 3 depicts exposure of drug as function of dose with measurements taken at 5 min and 60 min post dose on each of several days of twice-weekly administration over a 26 day period, and shows that drug exposure stabilizes by the third or fourth dose administered.

Figure 4:
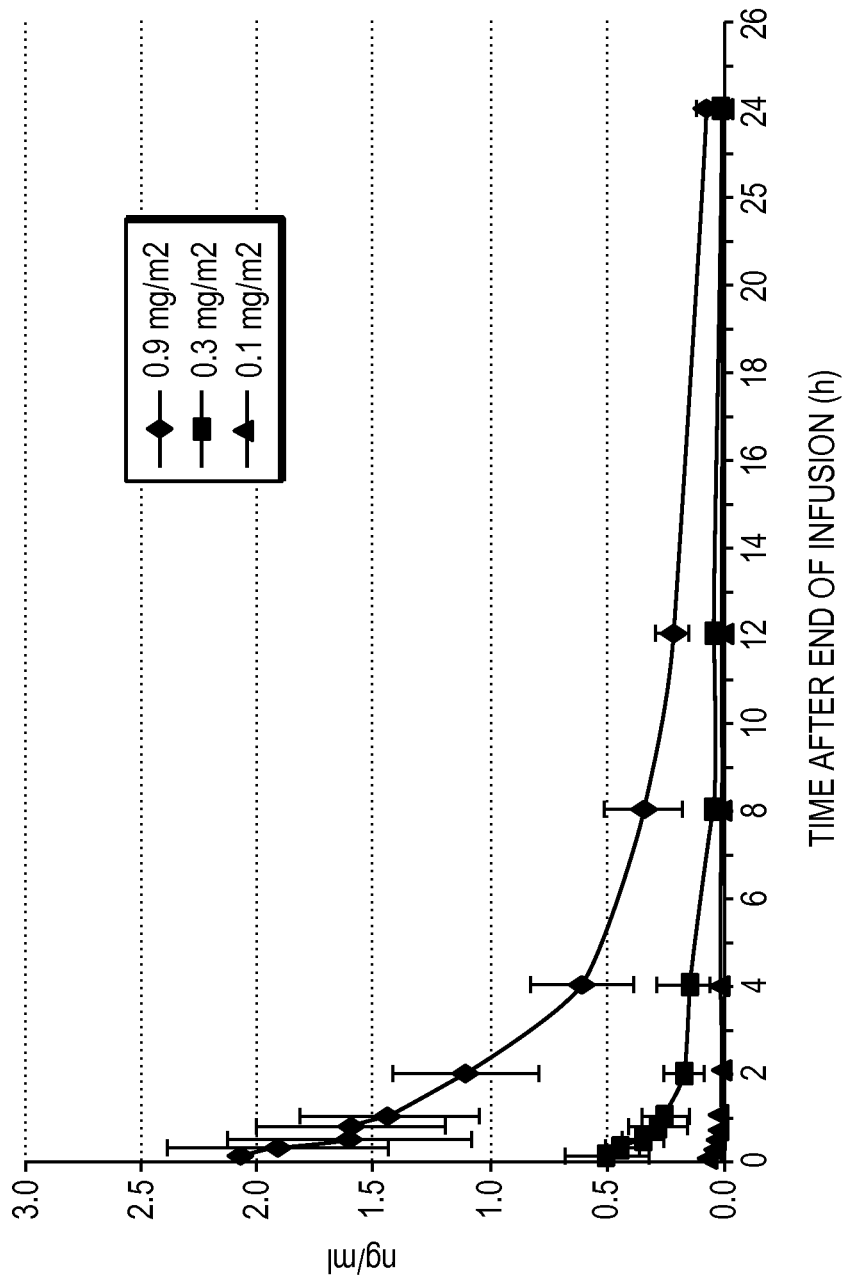
FIG. 4 shows average pharmacokinetic (PK) profile with dose (ng/ml) of drug at day 26 of trials participants receiving 0.1, 0.3 and 0.9 mg/m$^2$.
Figure 5:
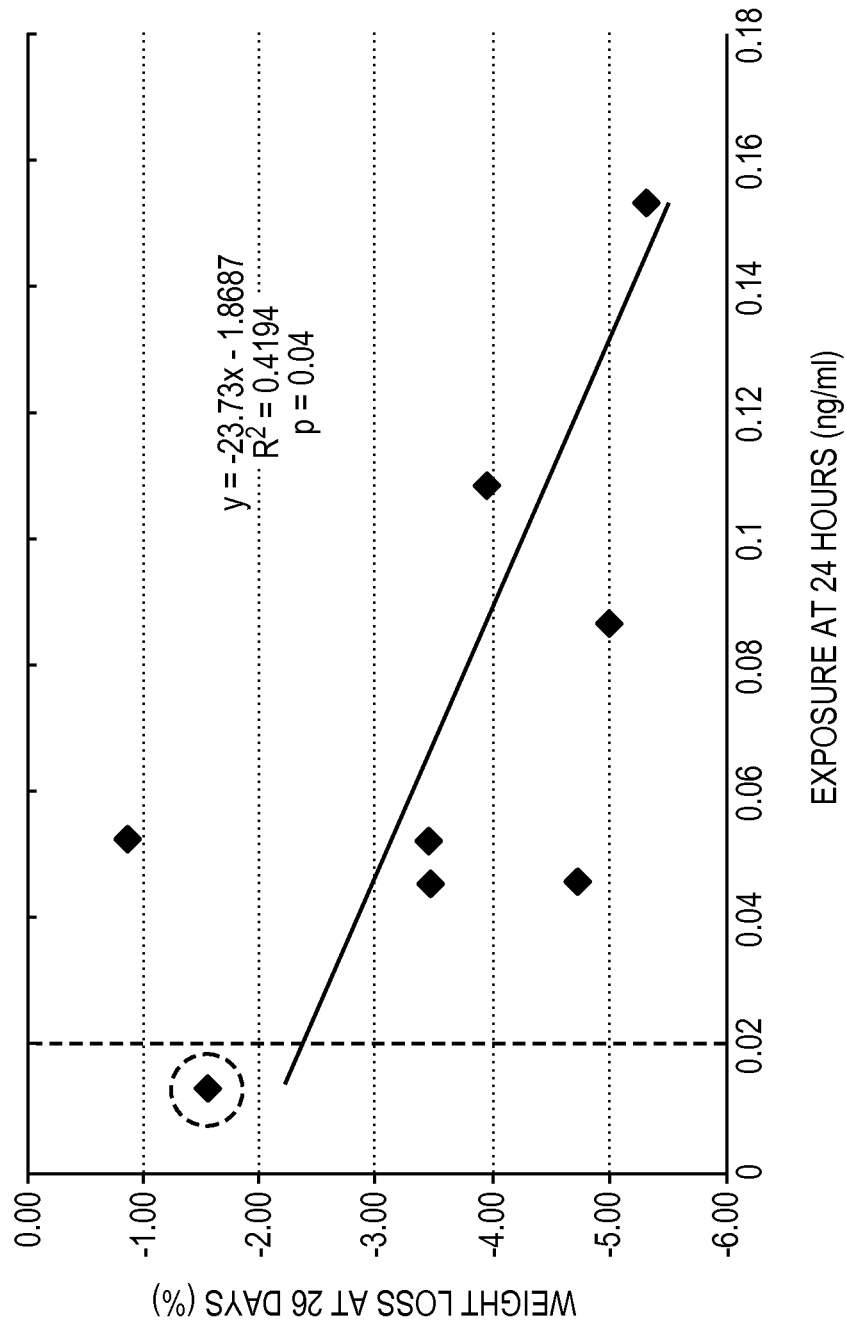
FIG. 5 depicts correlation of weight change and exposure of drug at 24 hours.

There was a significant correlation between weight loss of patients and maintained exposure of 0.02 ng/mL of the drug above the level of quantitation of the assay 24 hours after dosing, as shown in FIG. 4 (circled data point is exposure of one poor responder below the level of quantitation of assay). The PK profile at day 26 is representative of steady state (see FIG. 5). Lack of efficacy at 0.1 and 0.3 mg/m² supports maintaining drug exposure above 0.02 ng/mL at 24 hours post dose, but with no drug exposure 36 hours after dosing.

Example 2

Correlation of Effective Dose and Excess Body Weight

Figure 6:
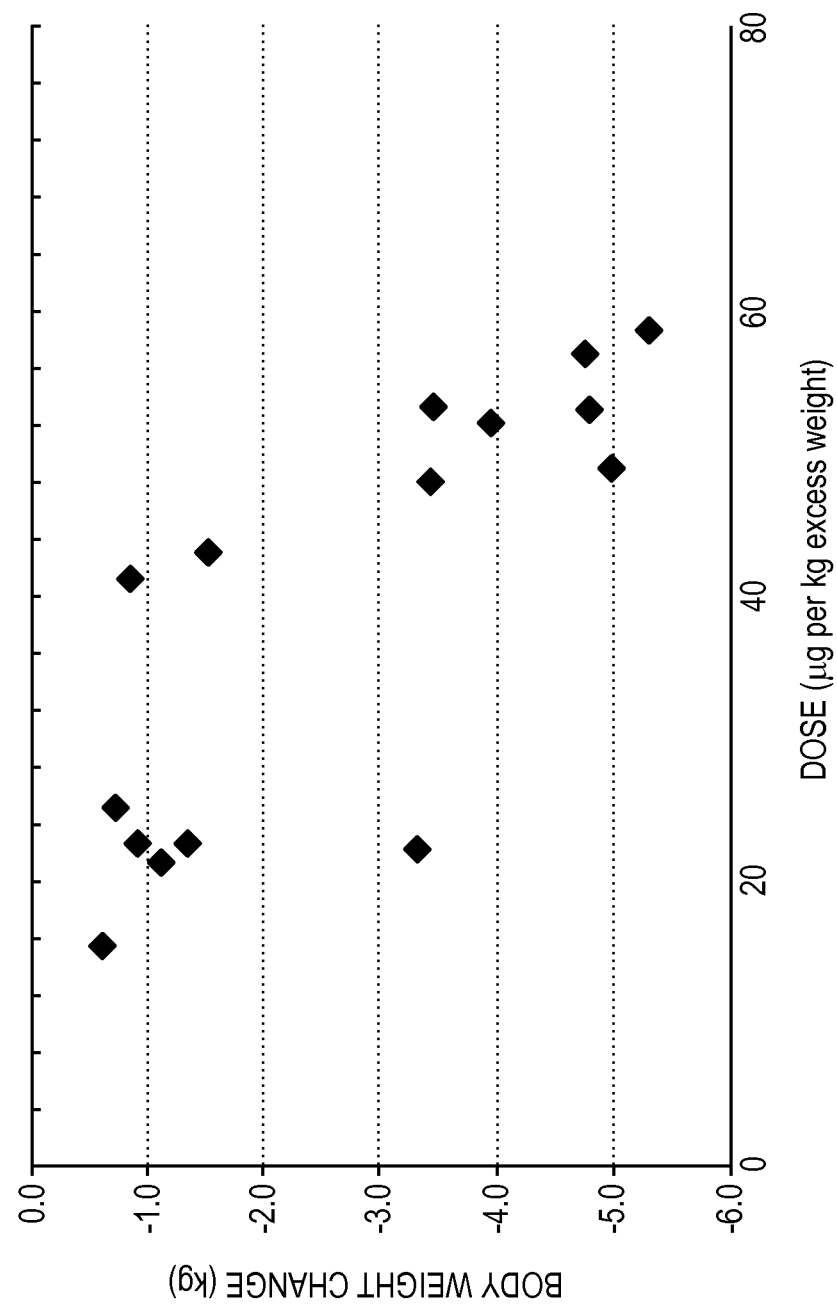
FIG. 6 depicts the body weight change (kg) as a function of a μg per kg excess weight dose of 6-O-(4-dimethylaminoethoxy)cinnamoyl fumagillol in obese human patients. X axis is dose of compound (μg/kg of excessive weight).

All of the subjects of the trial described in Example 1 received doses ranging from 1.8 to 2.2 mg with each administration (given twice weekly). However, weight change was not strictly associated with dose delivered. Instead, response was strongly associated with dose administered per unit excess body weight, as compared to weight change associated with dose delivered per unit body weight. FIG. 6 indicates the body weight change of patients in the combined 0.1 and 0.3 mg/m² cohorts vs. dose of compound in μg per kg excess weight of patient, and indicates that exceeding approximately 40 μg of drug per kg of excess body weight may be important in order to see effects in obese patients.

This correlation may be due to obtaining the drug effect at least in part by exposure of the drug to adipose tissue. This indicates that dosing appropriately with a MetAP2 inhibitor surprisingly requires consideration of a patient's excess weight (instead of total weight), given that drug exposures (drug amount) were not substantially different between subjects and both the vasculature and liver were dosed equivalently, but weight loss differed.

Figure 7:
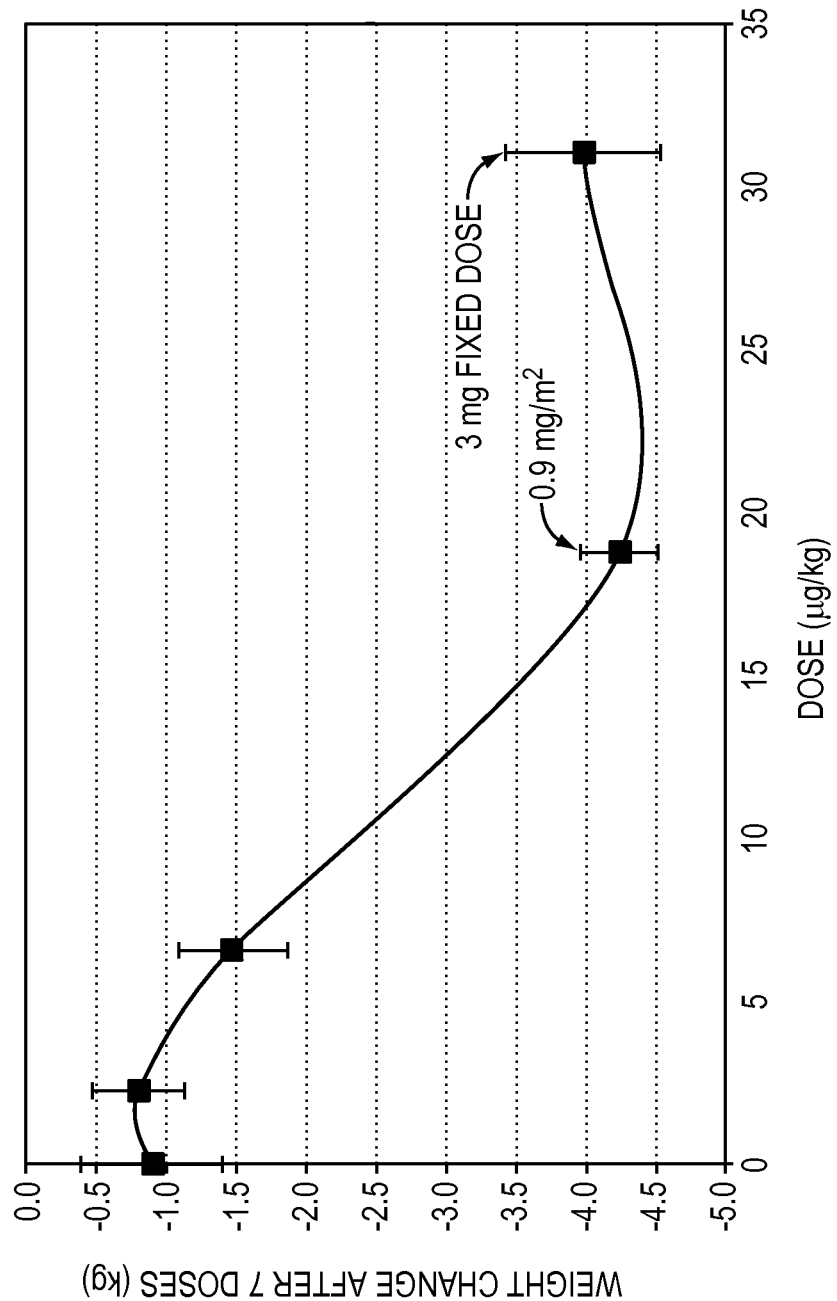
FIG. 7 depicts weight change in patients administered a twice a week dose of 6-O-(4-dimethylaminoethoxy)cinnamoyl fumagillol, with varied dosage amounts. Weight loss plateaus at 0.9 mg/m$^2$ (~1.8 mg dose) administered twice weekly, with a maximum efficacy obtained with a dose administered biweekly of ~20 μg/kg.

FIG. 7 indicates that weight loss efficacy is obtained at doses of ~20 μg/kg, and above, administered twice weekly.

Example 3

Adiponectin Levels

Levels of adiponectin in the serum of patients undergoing the trial were also measured. Adiponectin concentrations were markedly increased (by over 60%, see FIG. 8) with treatment, also pointing to the importance of adipose as a target for the drug since adiponectin is produced by fat cells.

Figure 8:
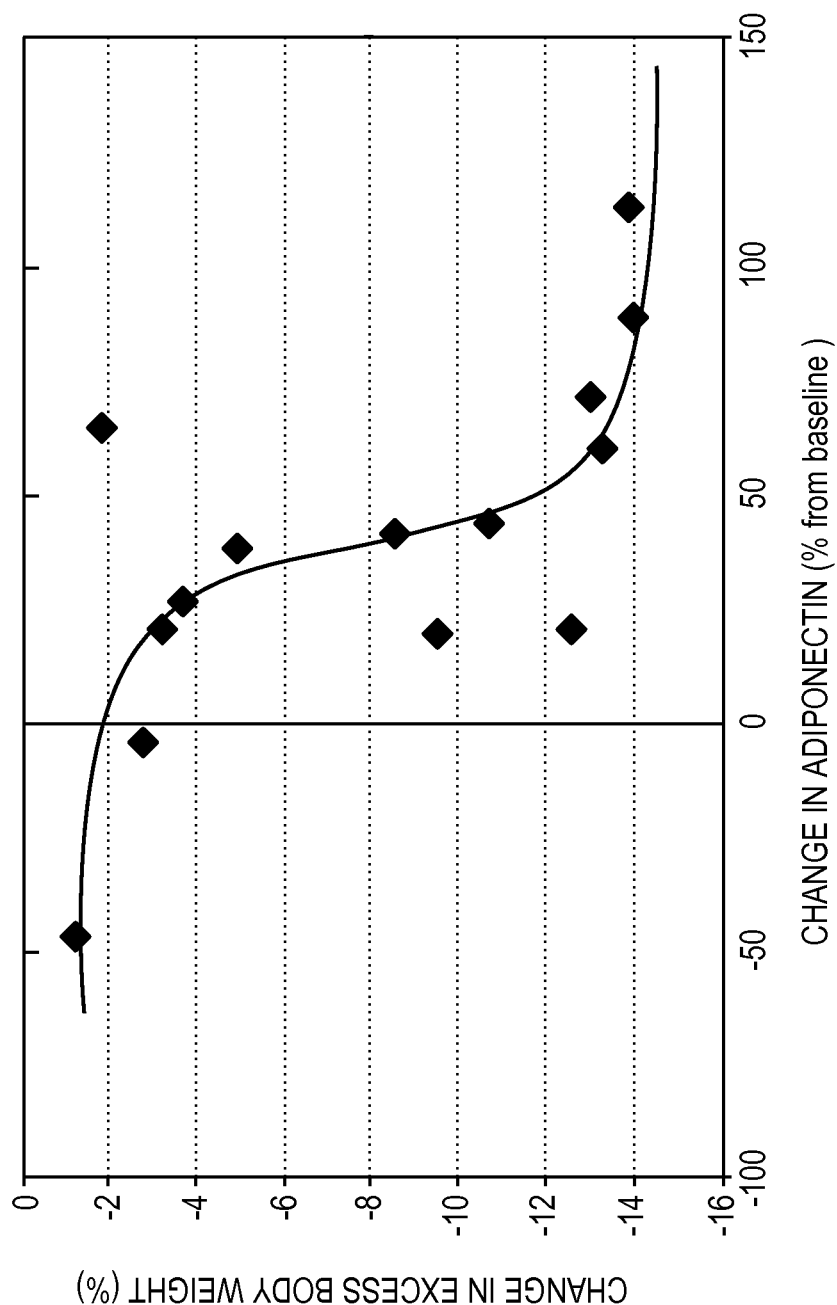
FIG. 8 depicts the correlation between adiponectin changes and excess weight loss after administration of the disclosed MetAP-2 inhibitor in human obese patients.

FIG. 8 also indicates that there is a strong correlation between adiponectin changes and excess weight loss.

Figure 9:
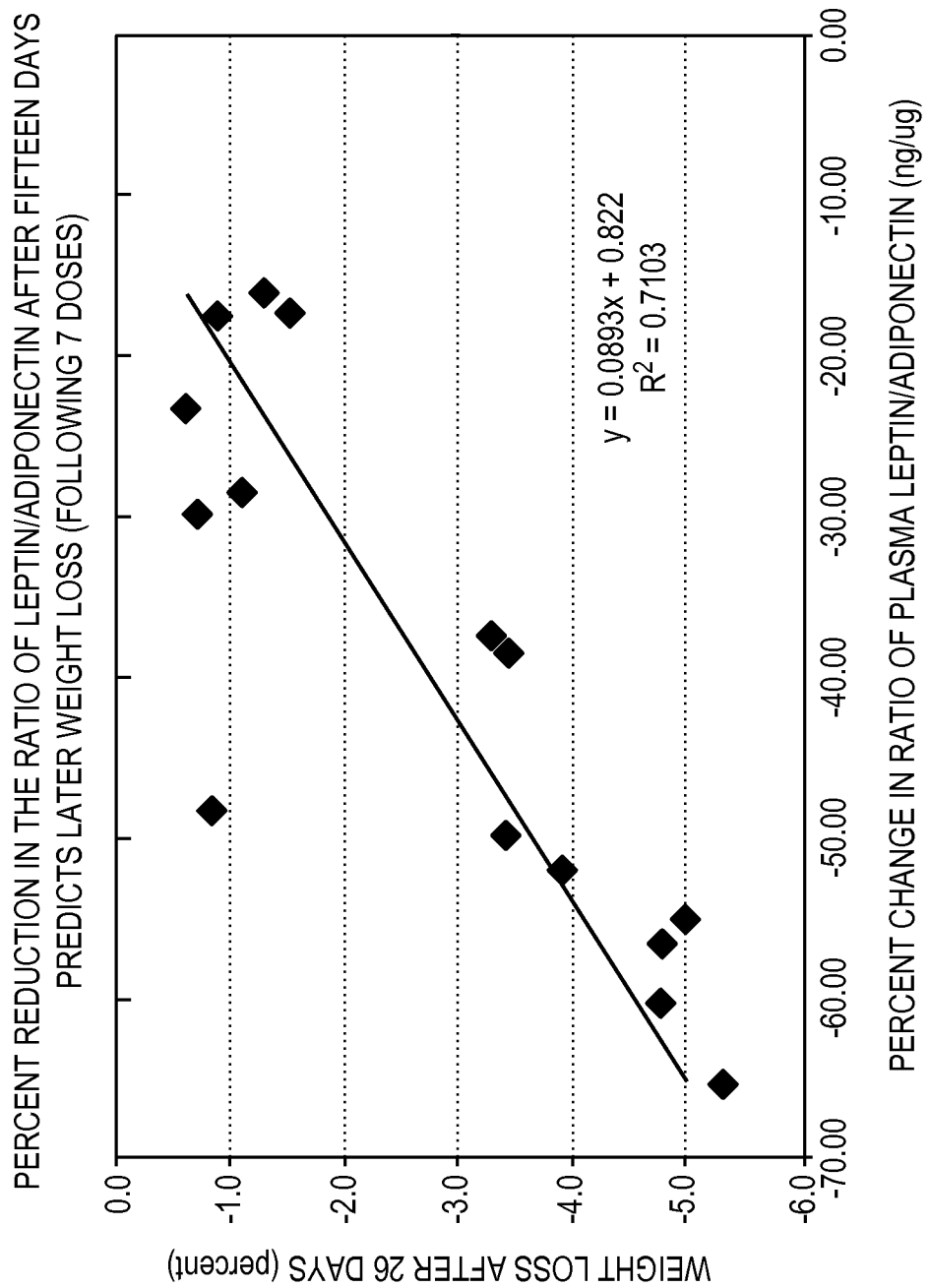
FIG. 9 depicts the effect of administration of the disclosed MetAP-2 inhibitor on the ratio of leptin to adiponectin serum levels in human obese patients after administration.

FIG. 9 indicates the changes in the ratio of two adipocyte factors (leptin and adiponectin) for subjects in the 0.3 and 0.9 mg/m$^2$ cohorts after 26 days of the trial. The effect of treatment on the ratio of leptin to adiponectin appears to be a particularly strong predictor of weight. Combined, these observations appear to indicate that adipose tissue is a critical target related to weight loss, and that targeting fat tissue for MetAP2 inhibitors or dosing to achieve optimal fat tissue exposure is important.

Example 4

Toxicity Studies

A testis toxicity study was performed using daily subcutaneous administration or every other day (every third day) subcutaneous administration in rats. 1 mg/kg of 6-O-(4-dimethylaminoethoxy)cinnamoyl fumagillol oxalate (Compound) was administered daily and compared to every third day with the same dose. Additionally, equivalent total exposure using a 3 mg/kg dose administered every third day was compared as well.

64 Sprague-Dawley male rats within ±20% of mean body weight at initiation of dosing were used for the study. Vehicle control or Compound was administered once daily or every 3$^{rd}$ day for 4 weeks, at a volume of 5 mL/kg, as follows, with groups 1-4 for toxicity and groups 5-8 for toxicokinetic studies.

| Group | Sex | Number | Dose Frequency | Dose Volume (mL/kg) | Dose (mg/kg) |
|---|---|---|---|---|---|
| 1 | Male | 10 | Daily | 5 | 0 |
| 2 | Male | 10 | Daily | 5 | 1 |
| 3 | Male | 10 | Every 3$^{rd}$ day | 5 | 1 |
| 4 | Male | 10 | Every 3$^{rd}$ day | 5 | 3 |
| 5 | Male | 6 | Daily | 5 | 0 |
| 6 | Male | 6 | Daily | 5 | 1 |
| 7 | Male | 6 | Every 3$^{rd}$ day | 5 | 5 |
| 8 | Male | 6 | Every 3$^{rd}$ day | 5 | 3 |

Upon completion of the study, complete necropsy examinations are performed, and the seminal vesicle, testes, and other organs are weighed at terminal necropsy. Terminal body weights are determined just prior to necropsy for assessment of organ weight changes.

Figure 10:
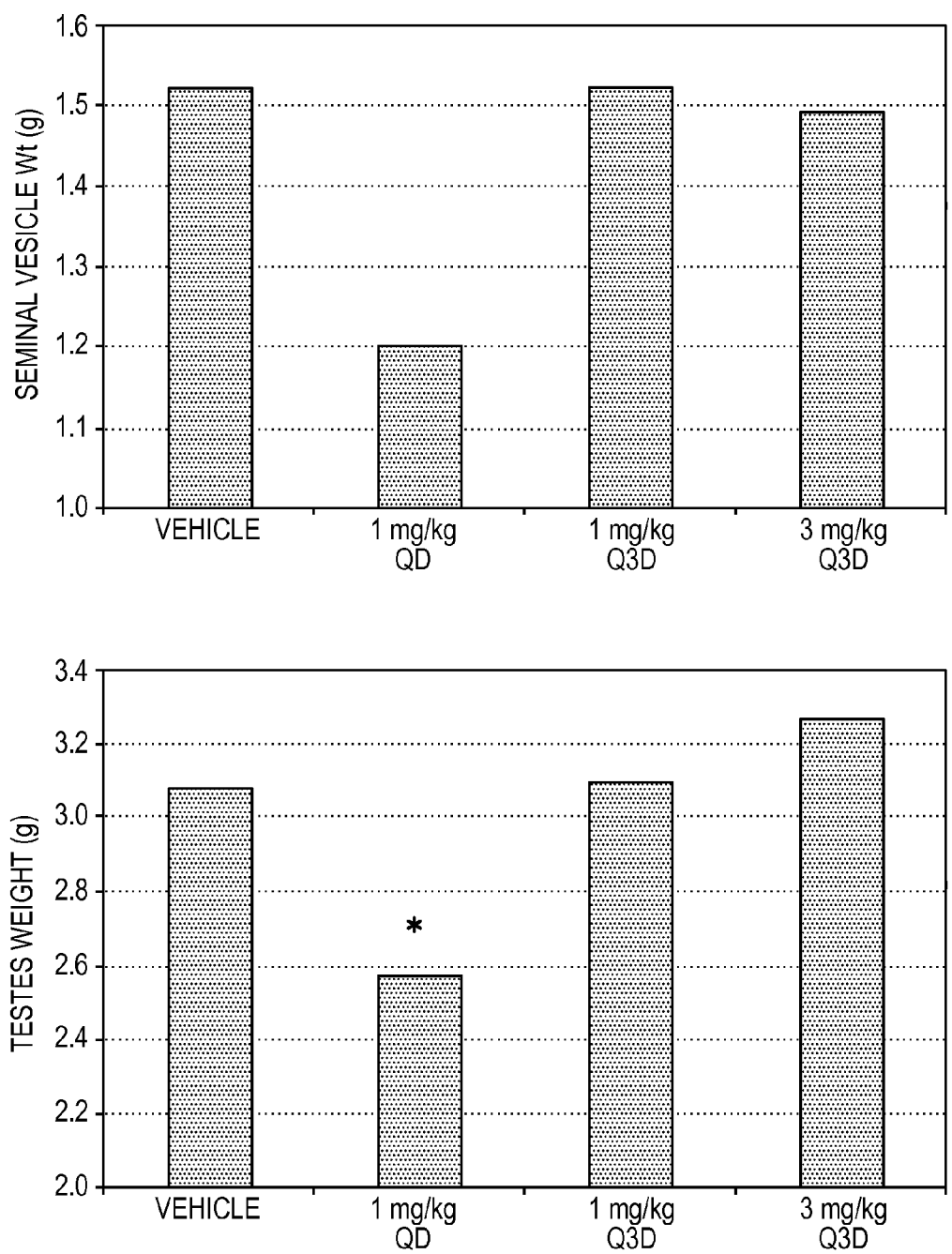
FIG. 10 depicts the seminal vesicle weight and testes weight in rats after daily or every three days indicating a less than daily dosing safety window.

Organ weight changes are shown in Table 2 and FIG. 10.

TABLE 2

| Organ | Group mg/kg | Absolute weight (g) | Relative to Bodyweight (%) | Relative to Brain Weight (%) |
|---|---|---|---|---|
| Thymus | 0 | 0.397 | 0.100 | 18.85 |
|  | 1 | 0.343 | 0.103 | 16.65 |
|  | 1 every 3$^{rd}$ day | 0.421 | 0.106 | 20.30 |
|  | 3 every 3$^{rd}$ day | 0.423 | 0.110 | 20.32 |
| Seminal Vesicles | 0 | 1.524 | 0.387 | 72.44 |
|  | 1 | 1.201** | 0.360 | 58.47 |
|  | 1 every 3$^{rd}$ day | 1.523 | 0.385 | 73.41 |
|  | 3 every 3$^{rd}$ day | 1.491 | 0.390 | 71.67 |
| Prostate | 0 | 0.658 | 0.167 | 31.38 |
|  | 1 | 0.546 | 0.163 | 26.59 |
|  | 1 every 3$^{rd}$ day | 0.710 | 0.179 | 34.13 |
|  | 3 every 3$^{rd}$ day | 0.663 | 0.172 | 31.88 |
| Epididymides | 0 | 1.278 | 0.324 | 60.75 |
|  | 1 | 1.130 | 0.338 | 55.30 |

TABLE 2-continued

| Organ | Group mg/kg | Absolute weight (g) | Relative to Bodyweight (%) | Relative to Brain Weight (%) |
|---|---|---|---|---|
|  | 1 every 3$^{rd}$ day | 1.249 | 0.317 | 60.09 |
|  | 3 every 3$^{rd}$ day | 1.267 | 0.331 | 60.80 |
| Testes | 0 | 3.080 | 0.781 | 146.41 |
|  | 1 | 2.569* | 0.769 | 125.72 |
|  | 1 every 3rd day | 3.097 | 0.786 | 149.04 |
|  | 3 every 3rd day | 3.273 | 0.856 | 157.22 |

*Significant (p < 0.05)
**Significant (p < 0.01)

As FIG. 10 shows, no tissue weight effects (testes and seminal vesicle weights) are observed in animals administered with less frequent dosing, indicating minimal or no testicular toxicity.

Table 3 shows the surprising findings from the study comparing 1 mg/kg/day dose with 1 mg/kg and 3 mg/kg every three days. While the 1 mg/kg/day dose indicates adverse findings (e.g. blood dyscrasias and/or irreversible testis lesions); the 3 mg/kg every three days does not show any significant adverse findings while reduces animal weight significantly, and increases the therapeutic window over prior findings using daily administration. The injection site tolerability appears to be acceptable even at doses up to 6 mg.

TABLE 3

| Findings | 1 mg/kg/day | 1 mg/kg Q3D | 3 mg/kg Q3D* |
|---|---|---|---|
| Hematology | Reduced blood cell counts WBC (0.68X), Lymphocyte (0.65X) Neutrophil (0.83X), Monocyte (0.79X), Eosinophil (0.75X), Basophil (0.55X), Large unstained cell (0.67X) | No findings | No findings |
| Clinical Chemistry | Reduced alk phos (0.72X) Reduced Inorg phosphate (0.96 X) Higher albumin/globulin (1.12X) Higher potassium (1.2X) | No findings | Higher albumin/globulin (1.09X) |
| Organ weight | Altered organ weights: Testes (0.83X), Epididymides (0.88X) Prostate (0.83X), Seminal vesicle (0.79X), Spleen (0.71X), Liver 0.85X, Salivary gland (0.87X), Thymus (0.86X), Thyroid (0.82X), Brain 1.15X, Adrenal (1.24X) | No findings | No findings |
| Macroscopic | Smaller testes and epididymides | No findings | No findings |
| Microscopic | Germ cell depletion/degeneration 9/10 Hypospermia (majority) Lymph node atrophy | No findings | No findings |

QD: Daily Administration; Q3D: every third day administration

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for treating obesity or for reducing body weight in a human patient having an initial body mass index at least about 30 kg/m$^2$, or at least about 27 kg/m$^2$ and suffering from weight related co-morbidity, and in need thereof, comprising parenterally administering to said patient, once or twice weekly, a dose of a formulation comprising about 0.5 mg/m$^2$ to about 3 mg/m$^2$, based on the patients actual or calculated surface area, of 6-O-(4-dimethylaminoethoxy)cinnamoyl fumagillol or pharmaceutically acceptable salts thereof.

2. The method of claim 1, wherein after administration of one or two doses, the patient has a body weight loss of about 0.3% to about 2% or more of the initial patient weight.

3. The method of claim 1, wherein parenterally administering is subcutaneous administering.

4. The method of claim 1, wherein parenterally administering is intravenous administering.

5. The method of claim 1, wherein the dose comprises about 0.5 mg/m$^2$ to about 1.5 mg/m$^2$.

6. The method of claim 1, wherein the therapeutically effective amount is about 0.9 mg/m$_2$.

7. A method for treating obesity or for reducing body weight in a human patient having an initial body mass index at least about 30 kg/m$^2$, or at least about 27 kg/m$^2$ and suffering from weight related co-morbidity, and in need thereof, comprising subcutaneously administering to said patient, once or twice weekly, a dose of a formulation comprising about 0.5 mg/m$^2$ to about 3 mg/m$^2$ of 6-0-(4-dimethylaminoethoxy)cinnamoyl fumagillol or pharmaceutically acceptable salts thereof.

8. The method of claim 7, wherein administering to the patient once or twice weekly is repeated until a desired weight is achieved.

9. The method of claim 8, wherein the dose comprises about 0.75 mg/m$^2$ to about 3 mg/m$^2$.

10. A method for reducing the weight of a human patient having an initial body mass index of at least about 30 kg/m$^2$, or at least about 27 kg/m$^2$ and suffering from weight related co-morbidity, comprising parenterally administering to said patient on a weekly, twice weekly, or every 3 or 4 days basis, a single dose of a parenteral formulation comprising a therapeutically effective amount of a compound 6-O-(4-dimethylaminoethoxy) cinnamoylfumagillol or pharmaceutically acceptable salts thereof.

11. The method of claim 10, wherein the dose comprises about 0.5 mg/m$^2$ to about 1.5 mg/m$^2$.

12. A method for treating obesity or for reducing body weight in a human patient having an initial body mass index at least about 30 kg/m$^2$, or at least about 27 kg/m$^2$ and suffering from weight related co-morbidity, and in need thereof, comprising parenterally administering to said patient, once or twice weekly, a dose of a formulation comprising about 1.8 mg of 6-O-(4-dimethylaminoethoxy)cinnamoyl fumagillol or pharmaceutically acceptable salts thereof.

* * * * *

UNITED STATES PATENT AND TRADEMARK OFFICE
CERTIFICATE OF CORRECTION

PATENT NO. : 9,000,035 B2  
APPLICATION NO. : 14/056829  
DATED : April 7, 2015  
INVENTOR(S) : Thomas E. Hughes It is certified that error appears in the above-identified patent and that said Letters Patent is hereby corrected as shown below:

In the claims

In claim 6, at column 17, line 25, replace "0.9mg/m$_2$" with -- 0.9mg/m$^2$ --

In claim 10, at column 18, line 17, replace "cinnamoylfumagillol" with -- cinnamoyl fumagillol --

Signed and Sealed this  
First Day of December, 2015

Michelle K. Lee  
*Director of the United States Patent and Trademark Office*